(12) United States Patent
Anderson et al.

(10) Patent No.: US 7,771,412 B2
(45) Date of Patent: Aug. 10, 2010

(54) ENVIRONMENTAL SEAL FOR FLUID DELIVERY DEVICE

(75) Inventors: Marc Anderson, Clinton, MA (US); John Garibotto, Marblehead, MA (US); Steven Dilanni, Danvers, MA (US)

(73) Assignee: Insulet Corporation, Bedford, MA (US)

( * ) Notice: Subject to any disclaimer, the term of this patent is extended or adjusted under 35 U.S.C. 154(b) by 212 days.

(21) Appl. No.: 11/874,776

(22) Filed: Oct. 18, 2007

(65) Prior Publication Data

US 2008/0116647 A1 May 22, 2008

Related U.S. Application Data

(60) Provisional application No. 60/829,984, filed on Oct. 18, 2006.

(51) Int. Cl.
*A61M 25/16* (2006.01)
(52) U.S. Cl. ..................... 604/533
(58) Field of Classification Search ............. 604/533, 604/284
See application file for complete search history.

(56) References Cited

U.S. PATENT DOCUMENTS

| | | | | |
|---|---|---|---|---|
| 2,667,986 | A * | 2/1954 | Perelson | 215/228 |
| 5,613,956 | A * | 3/1997 | Patterson et al. | 604/256 |
| 5,921,419 | A * | 7/1999 | Niedospial et al. | 215/247 |
| 5,954,694 | A * | 9/1999 | Sunseri | 604/96.01 |
| 6,050,978 | A * | 4/2000 | Orr et al. | 604/249 |
| 6,090,092 | A * | 7/2000 | Fowles et al. | 604/413 |
| 6,569,125 | B2 * | 5/2003 | Jepson et al. | 604/201 |
| 6,666,852 | B2 * | 12/2003 | Niedospial, Jr. | 604/415 |
| 6,699,221 | B2 * | 3/2004 | Vaillancourt | 604/167.01 |
| 6,883,778 | B1 * | 4/2005 | Newton et al. | 251/149.1 |
| 7,008,404 | B2 * | 3/2006 | Nakajima | 604/158 |
| 7,025,744 | B2 * | 4/2006 | Utterberg et al. | 604/83 |
| 7,160,272 | B1 * | 1/2007 | Eyal et al. | 604/249 |
| 2001/0053895 | A1 * | 12/2001 | Vaillancourt | 604/243 |
| 2002/0066715 | A1 * | 6/2002 | Niedospial, Jr. | 215/311 |
| 2005/0187524 | A1 * | 8/2005 | Willis et al. | 604/256 |
| 2007/0025811 | A1 * | 2/2007 | Wilhelm | 403/300 |
| 2007/0112332 | A1 * | 5/2007 | Harding et al. | 604/533 |
| 2008/0065000 | A1 * | 3/2008 | Bidinger et al. | 604/9 |
| 2008/0132880 | A1 * | 6/2008 | Buchman | 604/533 |
| 2008/0249508 | A1 * | 10/2008 | Lopez et al. | 604/533 |
| 2008/0287906 | A1 * | 11/2008 | Burkholz et al. | 604/500 |

* cited by examiner

*Primary Examiner*—Nicholas D Lucchesi
*Assistant Examiner*—Diva Ranade
(74) *Attorney, Agent, or Firm*—Grossman Tucker Perreault & Pfleger, PLLC

(57) ABSTRACT

An environmental seal for a fluid delivery device may include a 2-shot molded cap including a carrier and a low durometer silicone plug. The seal also may include a cap receptacle that applies compressive force to the plug displacing the plug material and forming a seal between the cap, the plug and the cap receptacle. A cannula may be slidably received in the plug and may move freely through the plug without compromising the seal.

19 Claims, 3 Drawing Sheets

ENVIRONMENTAL SEAL FOR FLUID DELIVERY DEVICE

CROSS-REFERENCE TO RELATED APPLICATION

The present application claims the benefit of U.S. Provisional Patent Application Ser. No. 60/829,984 filed Oct. 18, 2006, which is fully incorporated herein by reference.

TECHNICAL FIELD

The present invention relates to fluid delivery devices and more particularly, to an environmental seal in the fluid pathway of a fluid delivery device.

BACKGROUND INFORMATION

Among fluid delivery devices, especially for medical applications, there is often a need to provide an environmental seal around a fluid pathway as it passes from one environment to another and/or where one cannula portion is joined to another. Such an environmental seal might, for example, serve to exclude water from the interior of a device, such as an infusion pump. Such an environmental seal might also serve to exclude the passage of air from one environment to another to limit the transmission of microorganisms from one environment to another, or to maintain the integrity of the fluid pathway at the junction between two cannulas forming the pathway. It is well known to create such an environmental seal by inserting a pierceable membrane in a carrier element. However, since it is often desirable to make medical devices as small as possible, there is a corresponding need to make an environmental seal as small as possible without compromising the quality and reliability of the seal. Further, since such seals may be useful in devices that are intended to have short useful lives, it is also desirable to manufacture such devices at the lowest possible cost. Unfortunately, known methods for assembling environmental seals are not well suited for miniaturization with high quality and reliability and low cost.

BRIEF DESCRIPTION OF THE DRAWINGS

These and other features and advantages will be better understood by reading the following detailed description, taken together with the drawings wherein.

DETAILED DESCRIPTION

Figure 1:
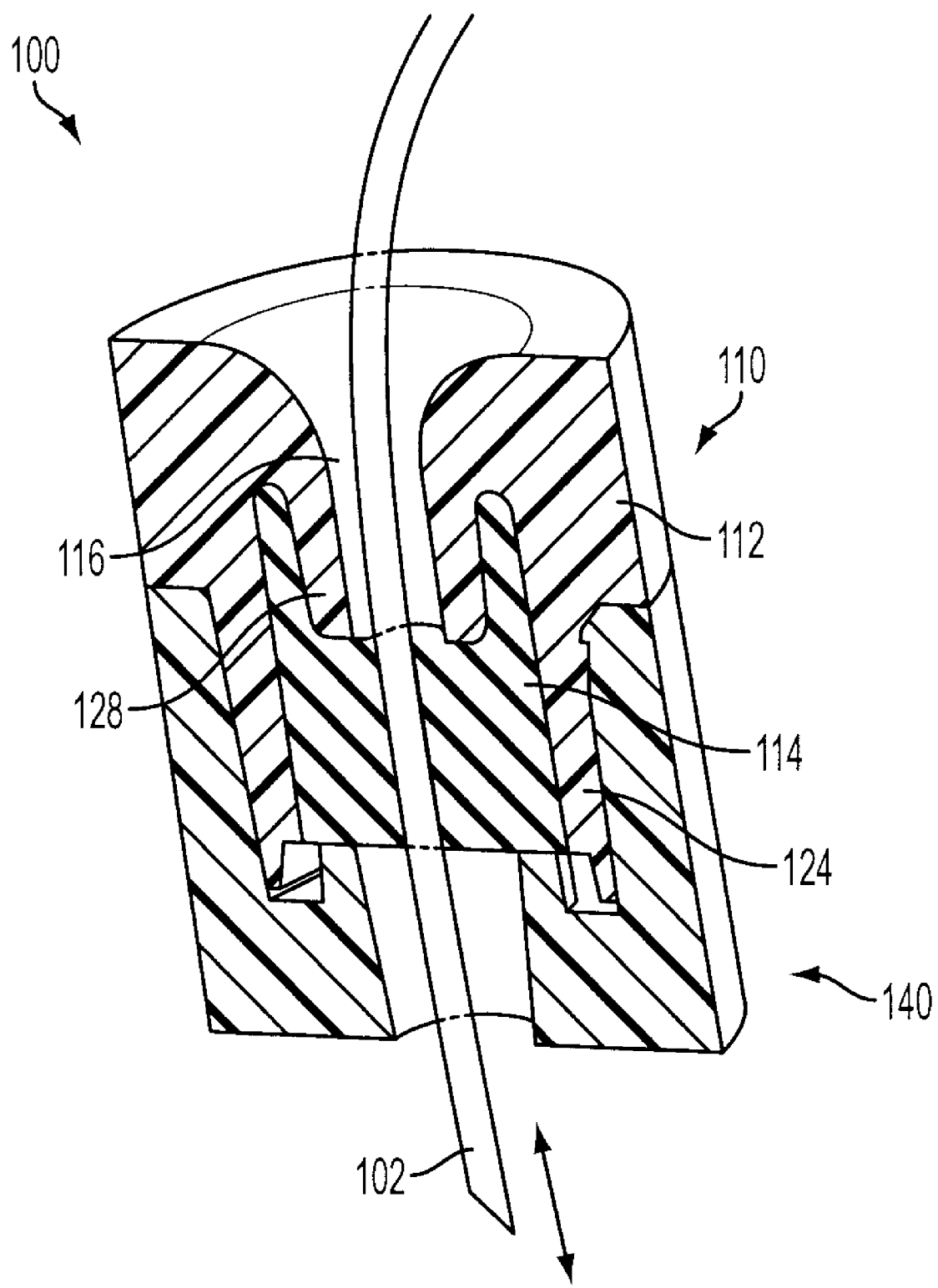
FIG. 1 is a cross section of an environmental seal, consistent with one embodiment of the present invention.
Figure 4:
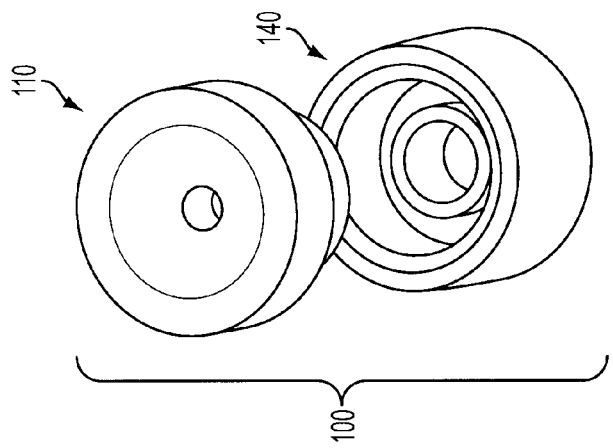
FIG. 4 is a top perspective view of the environmental seal shown in FIG. 1.
Figure 3:
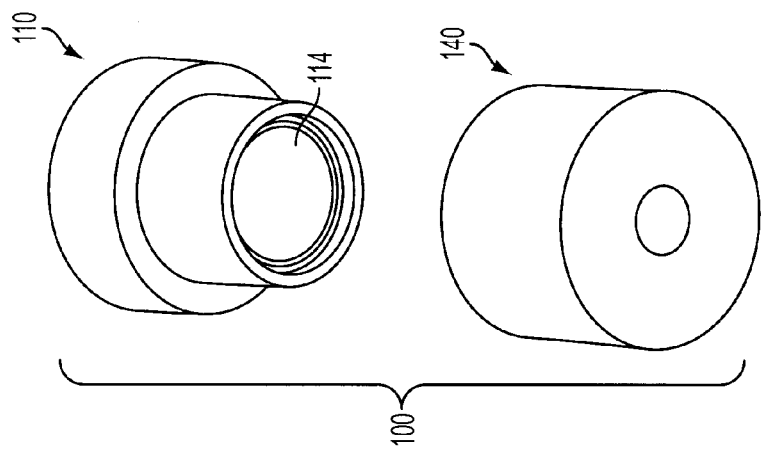
FIG. 3 is a bottom perspective view of the environmental seal shown in FIG. 1.
Figure 2:
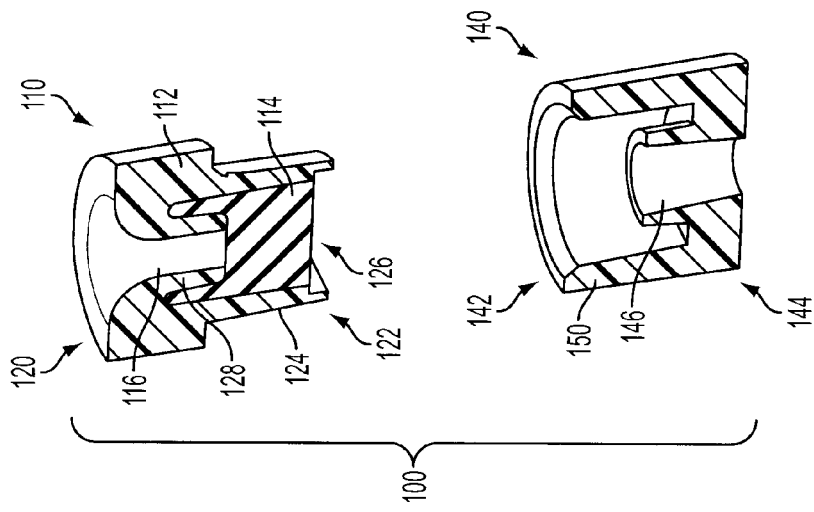
FIG. 2 is an exploded cross section of the environmental seal shown in FIG. 1.

Referring to FIGS. 1-4, the present invention is directed to an environmental seal 100 for a fluid delivery device. The environmental seal 100 may be configured to receive a cannula 102 or other similar structure providing a fluid pathway. The environmental seal 100 comprises a cap 110 comprising a carrier 112 and a plug 114. The carrier 112 is preferably a relatively high durometer molded plastic component having a solid form and a channel 116 through the solid. The carrier portion 112 of the cap 110 may have a cylindrical shape with the channel 116 passing from the proximal end 120 to the distal end 122. The distal end 122 of the carrier 112 may comprise a sleeve portion 124 surrounding the plug 114. The sleeve portion 124 preferably defines a widened area of the channel 116 forming a cavity 126 at the distal end 122 of the carrier 112. The carrier 112 may also comprise a circumferential flange 128 defining the narrow portion of the channel 116 and extending into the cavity 126 formed by the wide portion of the channel 116. The walls of the sleeve 124 may be tapered or contain other physical features to facilitate the cap 110 mating with the cap receptacle 140 described below.

The cap 110 also comprises a plug 114. The plug 114 may be formed of silicone, preferably having a durometer from about 5-15 SHORE A, most preferably 10 SHORE A. The plug 114 is preferably formed from a medical grade silicone and may be a bondable silicone. The plug 114 completely obstructs a portion of the channel 116. The plug 114 may be formed in the cavity 126 of the carrier 112. The cap 110 is preferably formed by a 2-shot molding process in which the carrier portion 112 comprises the first shot and the plug portion 114 comprises the second shot. The cap 110 may also be formed by molding the carrier 112 and pot curing the plug 114 in the carrier 112. The carrier 112 may contain one or more secondary channels (not shown) in which the silicone may be injection molded or pot cured and which serve to secure the plug 114 to the carrier 112.

The environmental seal 100 may also comprise a cap receptacle 140 that receives the cap 110 and applies a compressive force to a portion of the circumference of the cap 110. The cap receptacle 140 is adapted to mate with the cap 110. The cap receptacle 140 is a solid having proximal and distal ends 142, 144 and a channel 146 extending through the cap receptacle 140 from the proximal end 142 to the distal end 144. The proximal end 142 of the cap receptacle 140 comprises an outer sleeve portion 150 adapted to mate with the inner sleeve portion 124 of the cap 110 and to apply a compressive force to the inner sleeve portion 124 and the plug 114. The outer sleeve 150 of the cap receptacle 140 may be tapered to mate with the tapered sleeve 124 of the cap 110. Preferably, when the cap 110 and cap receptacle 140 are assembled, the plug 114, the inner sleeve 124 and the outer sleeve 150 are generally concentric cylinders.

When the cap 110 and cap receptacle 140 are assembled, the outer sleeve 150 of the cap receptacle 140 applies sufficient compression to the inner sleeve 124 of the cap 110 and plug 114 to create a fluid impervious seal around the cannula 102 while permitting movement of the cannula 102 through the plug 114 and the channel 116, as described below. In one embodiment, when the cap 110 and cap receptacle 140 are assembled, the outer sleeve 150 of the cap receptacle 140 applies sufficient compression to the inner sleeve 124 of the cap 110 and plug 114 to displace at least about 5% of the volume of the plug 114. Notably, since the plug 114 is made of silicone, it does not compress, but portions of the cap 110 are displaced to fill gaps between the cap 110 and cap receptacle 140 and thereby form a seal. The cap receptacle 140 may be integrated into a separate body. For example, the cap receptacle may be feature molded in the housing of an infusion pump (not shown).

The environmental seal 100 may also comprise a cannula 102 or similar structure passing through the channel 116 from the proximal end to the distal end and through the plug 114. When the cap 110, cap receptacle 140 and cannula 102 are assembled, the cannula 102 preferably can move relatively easily along the axis of the channel 116 through the plug 114, but the plug 114 forms a seal around the cannula 102 to exclude water and air from crossing from the distal to the proximal end of the environmental seal, or vice versa. The cannula 102 may be a single cannula or may comprise multiple lumens. In one embodiment, the cannula comprises a relatively stiff introducer needle surrounded by a flexible soft cannula.

Figure 5:
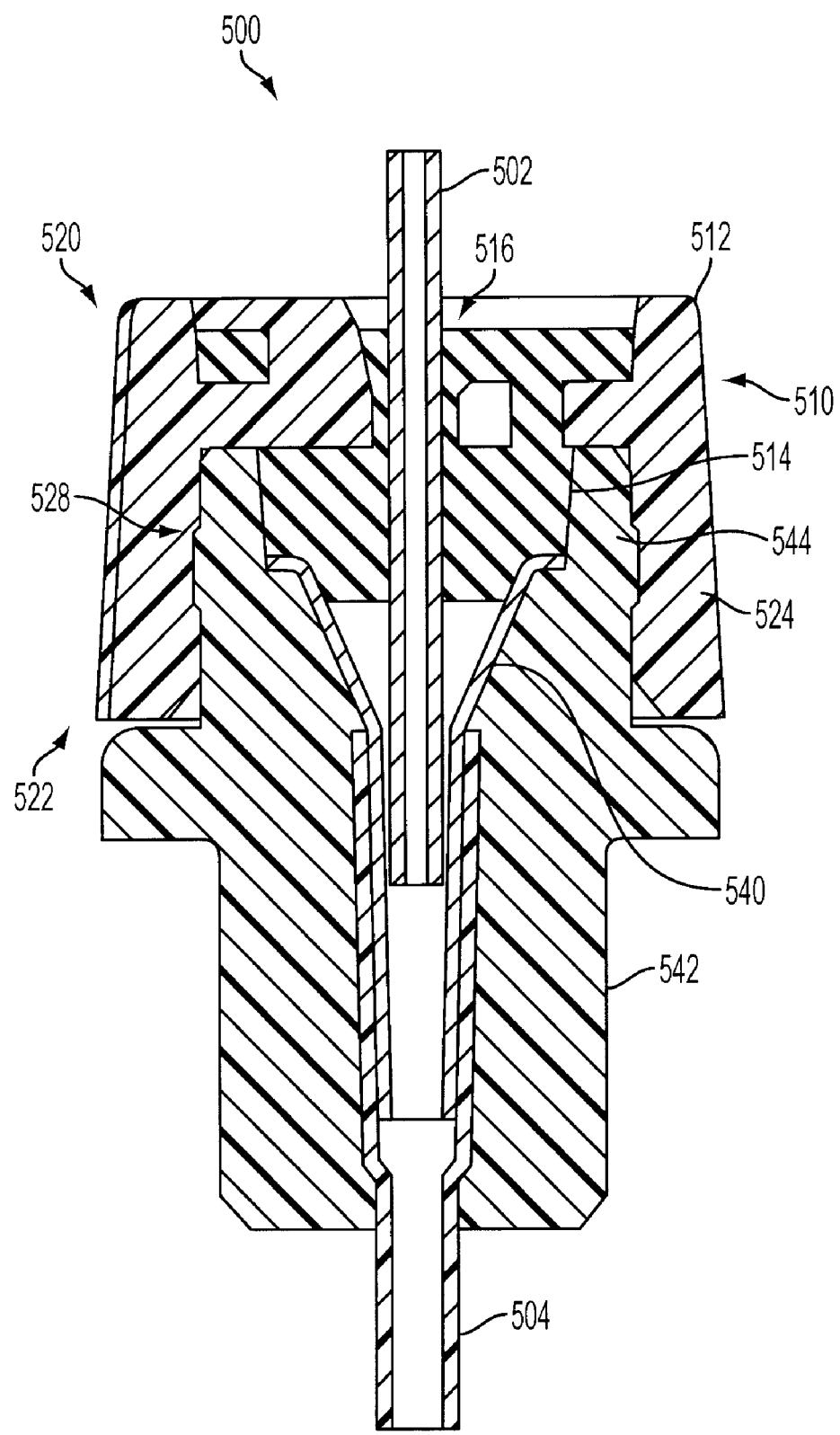
FIG. 5 is a cross section of a cannula seal consistent with another embodiment of the present invention.

Another embodiment of an environmental seal 500, shown in FIG. 5, serves as a junction between two cannula portions 502, 504 sealing the fluid pathway formed by the cannula portions 502, 504 from the environment outside the fluid pathway. In this embodiment, the seal 500 comprises a nozzle cap 510, a plug 514, a nozzle 540, a nozzle boss 542, the proximal cannula 502 and the distal cannula 504.

The nozzle cap 510 comprises a carrier 512 and a plug 514. The carrier 512 is preferably a relatively high durometer molded plastic component having a solid form and a channel 516 through the solid. The carrier portion 512 of the cap 510 may have a cylindrical shape with the channel 516 passing from the proximal end 520 to the distal end 522 of the carrier 512. The distal end 522 of the carrier 512 may comprise a sleeve portion 524 surrounding the plug 514. The sleeve portion 524 preferably defines a widened area of the channel 516 forming a cavity 528 at the distal end of the carrier 512. The walls of the sleeve 524 may be tapered or contain other physical features to facilitate the cap mating with the nozzle boss 542 described below.

The cap 510 also comprises a plug 514. The plug 514 may be formed of silicone, preferably having a durometer from about 5-15 SHORE A, most preferably 10 SHORE A. The plug 514 completely obstructs a narrow portion of the channel 516, but, unlike the embodiment of FIGS. 1-4 does not fill the cavity 528. The distal end of the plug 514 may be tapered to mate with the nozzle 540 and nozzle boss 542. The nozzle cap 510 is preferably formed by a 2-shot molding process in which the carrier portion 512 comprises the first shot and the plug portion 514 comprises the second shot. The nozzle cap 510 may also be formed by molding the carrier 512 and pot curing the plug 514 in the carrier 512. The carrier 512 may contain one or more secondary channels (not shown) in which the silicone may be injection molded or pot cured and which serve to secure the plug 514 to the carrier 512.

The environmental seal 500 also comprises a nozzle 540 and nozzle boss 542. The proximal end of the nozzle 540 is adapted to mate with the plug 514 and the nozzle boss 542 respectively. The distal end of the nozzle 540 is adapted to mate with the proximal end of the distal cannula 504, thereby securing the distal cannula 504 to the nozzle boss 542. The nozzle 540, as well as the proximal and distal cannulas 502, 504, are preferably made with a material that is compatible with the substance to be transferred through the cannulas 502, 504 and nozzle 540. In one embodiment, the nozzle 540 and proximal cannula 502 are made from stainless steel and the distal cannula 504 is made from fluorinated ethylene propylene.

As noted above, the nozzle boss 542 receives the distal cannula 504 and the nozzle 540. The proximal end of the nozzle boss 542 comprises a sleeve 544 adapted to mate with the inner walls of the sleeve 524 of the nozzle cap 510 such that the nozzle cap sleeve 524 applies a compressive force to the nozzle boss sleeve 544 and the plug 514 sufficient to cause the plug 514 to form a seal with the nozzle 540, nozzle boss 542 and nozzle cap carrier 512, but not so great as to inhibit movement of the proximal cannula 502 through the plug 514 along the axis of the channel 516. In one embodiment, when the nozzle cap 510, nozzle 540 and nozzle boss 542 are assembled, the nozzle cap sleeve 524 applies sufficient compression to the nozzle boss sleeve 544, and, thereby, the plug 514 to displace at least about 5% of the volume of the plug 514.

In an embodiment, the environmental seal 500 is part of cannula insertion system in which the proximal cannula 502 is held by a first moveable carrier (not shown) and the distal cannula 504 is received in the nozzle boss 542, which is held by a second moveable carrier (not shown). In use, the first and second carriers may be advanced to an advanced position such that the proximal and distal cannulas 502, 504 are advanced together to a desired position, such as a desired subcutaneous depth. Thereafter, the second moveable carrier is moved proximally thereby withdrawing the proximal cannula 502 a selected proximal distance. In this process, the proximal cannula 502 moves freely through the plug along the axis of the channel 516 without compromising the seal between the nozzle cap 510, plug 514, nozzle 540 and nozzle boss 542 so that there is no leakage into or out of the fluid pathway formed by the proximal and distal cannulas 502, 504 and the nozzle boss 542.

Accordingly, the environment seal, consistent with embodiments of the present invention, is capable of sealing a fluid pathway in a fluid delivery device while being relatively small and produced in accordance with relatively tight specifications and at relatively low cost.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. An environmental seal for a fluid delivery device, comprising:
    a cap comprising:
        a carrier portion including a proximal end and a distal end and a channel extending through the carrier from the proximal end to the distal end;
        a plug located in the solid carrier portion, the plug being configured to slidably receive a cannula therethrough; and
        wherein the cap is formed in a two-shot molding process such that a first shot forms the carrier portion and a second shot forms the plug in the carrier portion and obstructing the channel, wherein the carrier portion is formed from a material having a relatively high durometer and the plug is formed from a material having a relatively low durometer; and
    a cap receptacle configured to mate with the cap, wherein the cap receptacle includes a proximal end and a distal end and a channel extending through the cap receptacle from the proximal end to the distal end, wherein the distal end of the carrier portion comprises an inner sleeve surrounding the plug, and wherein the proximal end of the cap receptacle comprises an outer sleeve configured to mate with the inner sleeve of the carrier portion and to apply a compressive force to the inner sleeve and the plug.

2. The environmental seal of claim 1, wherein the channel includes a narrow portion and a wide portion that forms a cavity containing the plug.

3. The environmental seal of claim 2, wherein the carrier portion comprises a circumferential flange that defines the narrow portion of the channel and extends into the cavity formed by the wide portion.

4. The environmental seal of claim 3, wherein the plug, the inner sleeve and the outer sleeve are generally concentric cylinders.

5. The environmental seal of claim 3, wherein the plug is formed from a material having a durometer from about 5 SHORE A to about 15 SHORE A.

6. The environmental seal of claim 5, wherein the outer sleeve applies sufficient compression to the inner sleeve and the plug to displace the plug at least about 5% of the volume of the plug.

7. The environmental seal of claim 6, wherein the second shot material forming the plug is silicone.

8. The environmental seal of claim 3, further comprising a cannula passing through the channel and the plug.

9. The environmental seal of claim 8, wherein the outer sleeve applies sufficient compression to the inner sleeve to create a fluid impervious seal around the cannula while permitting movement of the cannula through the plug and the channel.

10. The environmental seal of claim 9, wherein the cannula comprises a first and second lumen wherein the first and second lumens are at least partially concentric.

11. The environmental seal of claim 1, wherein the plug is formed from a material having a durometer from about 5 SHORE A to about 15 SHORE A.

12. The environmental seal of claim 1, wherein the plug is formed from a material having a durometer of about 10 SHORE A.

13. An environmental seal for a fluid delivery device, comprising:
 a cap comprising:
  a solid carrier formed from a material having a first durometer, the solid carrier including a proximal end and a distal end and defining a channel extending from the proximal end to the distal end; and
  a solid plug formed from a material having a second durometer lower than the first durometer, the solid plug received in the solid carrier and obstructing the channel; and
 a cap receptacle configured to mate with the cap, wherein the cap receptacle includes a proximal end and a distal end and defines a channel extending from the proximal end to the distal end of the cap receptacle.

14. The environmental seal of claim 13, wherein the cap is formed in a 2-shot molding process in which the carrier is formed in the first shot and the plug is formed in the second shot.

15. A cannula seal comprising:
 a nozzle cap comprising a carrier and a plug located in a cavity of the carrier;
 a nozzle boss engaged with the nozzle cap;
 a nozzle received in the nozzle boss;
 a proximal cannula passing from a distal end of the nozzle cap through the plug and into the nozzle boss, wherein the plug forms a seal between the nozzle cap, the nozzle, the nozzle boss and the proximal cannula; and
 a distal cannula secured between the nozzle boss and the nozzle, wherein the distal cannula, the nozzle and the proximal cannula form a continuous fluid pathway that is sealed from the environment.

16. The cannula seal of claim 15, wherein the nozzle cap is a 2-shot molded component and wherein the carrier is formed from a relatively high durometer material in the first shot and the plug is formed of a relatively low durometer material in the second shot.

17. The cannula seal of claim 16, wherein the plug is formed of silicone having a durometer from about 5 SHORE A to about 15 SHORE A.

18. The cannula seal of claim 17, wherein the nozzle cap comprises a sleeve that mates with a sleeve of the nozzle boss, and wherein the sleeve of the nozzle boss mates with the plug such that the nozzle cap sleeve applies a compressive force to the nozzle boss sleeve, which applies a compressive force to the plug.

19. The cannula seal of claim 18 wherein the compressive force is sufficient to form a seal between the nozzle cap, the nozzle, the nozzle boss and the proximal cannula, but is not so great as to impede the movement of the proximal cannula through the plug along the axis of the carrier.

\* \* \* \* \*